United States Patent
Calabrese

(10) Patent No.: US 7,618,972 B2
(45) Date of Patent: Nov. 17, 2009

(54) SUBSTITUTED TRIAZOLE DERIVATIVES AS OXYTOCIN ANTAGONISTS

(75) Inventor: Andrew Antony Calabrese, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/909,290

(22) PCT Filed: Mar. 8, 2006

(86) PCT No.: PCT/IB2006/000602

§ 371 (c)(1),
(2), (4) Date: Nov. 19, 2007

(87) PCT Pub. No.: WO2006/100557

PCT Pub. Date: Sep. 28, 2006

(65) Prior Publication Data

US 2008/0167323 A1    Jul. 10, 2008

Related U.S. Application Data

(60) Provisional application No. 60/664,091, filed on Mar. 21, 2005.

(51) Int. Cl.
    *A61K 31/4965*    (2006.01)
(52) U.S. Cl. .................. 514/255.05; 544/336; 546/348; 548/266.2
(58) Field of Classification Search ............ 514/255.05; 544/336; 546/348; 548/266.2
    See application file for complete search history.

(56) References Cited

U.S. PATENT DOCUMENTS

| | | | | |
|---|---|---|---|---|
| 2,503,059 | A | 4/1950 | Miescher et al. | 260/309 |
| 2,599,000 | A | 6/1952 | Kerwin et al. | 260/570 |
| 3,381,009 | A | 4/1968 | Palazzo et al. | 260/268 |
| 3,511,836 | A | 5/1970 | Hans-Jurgen et al. | 260/256 |
| 3,527,761 | A | 9/1970 | Archibald et al. | 260/293 |
| 3,997,666 | A | 12/1976 | Witte et al. | 424/250 |
| 4,026,894 | A | 5/1977 | Winn et al. | 260/256 |
| 4,188,390 | A | 2/1980 | Campbell | 424/251 |
| 4,252,721 | A | 2/1981 | Silvestrini et al. | 260/243 |
| 4,315,007 | A | 2/1982 | Manoury | 424/251 |
| 4,703,063 | A | 10/1987 | Imai et al. | 514/603 |
| 5,698,560 | A | 12/1997 | Onoda et al. | 514/267 |
| 5,801,180 | A | 9/1998 | Takase et al. | 514/259 |
| 5,861,396 | A | 1/1999 | Niewohner et al. | |
| 5,945,117 | A | 8/1999 | El-Rashidy et al. | 424/430 |

FOREIGN PATENT DOCUMENTS

| | | |
|---|---|---|
| EP | 0526004 | 10/1997 |
| EP | 0995750 | 10/1999 |
| EP | 1092718 | 10/2000 |
| EP | 1092719 | 10/2000 |
| EP | 1097719 | 11/2000 |
| EP | 1293503 | 5/2001 |
| WO | WO9111172 | 8/1991 |
| WO | WO9312095 | 6/1993 |
| WO | WO9400453 | 1/1994 |
| WO | WO9492518 | 2/1994 |
| WO | WO9405661 | 3/1994 |
| WO | WO9415932 | 7/1994 |
| WO | WO9849166 | 11/1998 |
| WO | WO9902159 | 1/1999 |
| WO | WO9904433 | 1/1999 |
| WO | WO9954333 | 10/1999 |
| WO | WO0002550 | 1/2000 |
| WO | WO0024745 | 5/2000 |
| WO | WO0028993 | 5/2000 |
| WO | WO0035298 | 6/2000 |
| WO | WO0127112 | 4/2001 |
| WO | WO0127113 | 4/2001 |
| WO | WO0158880 | 8/2001 |
| WO | WO 2005/028452 | * 3/2005 |

OTHER PUBLICATIONS

Jordan, V. C. Nature Reviews: Drug Discovery, 2, 2003, p. 205.*
Chawla, et al. Curr. Res. & Info. Pharm. Sci. (CRIPS), 5, 1, 2004, pp. 9-12.*
Patani, et al. Chem. Rev., 96, 1996, pp. 3147-3176.*
Arletti, et al., *Peptides*, "Influence of oxytocin on feeding behavior in the rat.", 10(1), 89-93, (1989).
Berman, et al., *Urology* "Female sexual dysfunction: incidence, pathophysiology, evaluation, and treatment options", vol. 54(3), 385-91, (1999).
Finnin, et al., *Journal Pharm Science*, 'Transdermal Penetration Enhancers : Applications, Limitations, and potential', vol. 88 (10), 955-958, (1999).

(Continued)

*Primary Examiner*—James O Wilson
*Assistant Examiner*—Douglas M Willis
(74) *Attorney, Agent, or Firm*—Gregg C. Benson; John A. Wichtowski

(57) ABSTRACT

The present invention relates to a class of substituted triazoles of formula (I) with activity as oxytocin antagonists, uses thereof, processes for the preparation thereof and compositions containing said inhibitors. These inhibitors have utility in a variety of therapeutic areas including sexual dysfunction, particularly premature ejaculation (P.E.).

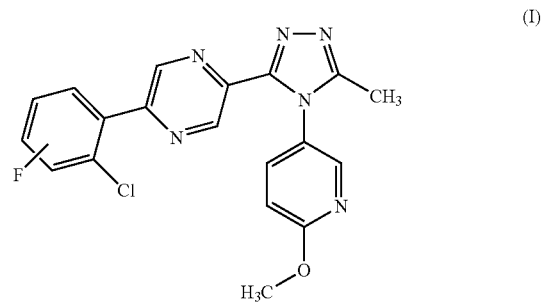

(I)

3 Claims, No Drawings

OTHER PUBLICATIONS

Gimpl, et al., *Physiological Reviews*, "The oxytocin receptor system: structure, function, and regulation." vol. 81(2), 629-683, (2001).

Leiblum S R, *International Journal of Impotence Research*, "Definition and classification of female sexual disorders" (1998), 10 Suppl 2 S104-6.

Liang, et al., *Expert Opinion in Therapeutic Patents*, "Fast-dissolving intraoral drug deliver system", vol. 11 (6), 981-986, (2001).

Melman, et al., *The Journal of Urology*, "The epidemiology and pathophysiology of erectile dysfunction." vol. 161(1), 5-11, (1999).

Nicholson, et al, *Advances in Experimental Medicine and Biology*, "Oxytocin and prostatic function." vol. 395(Oxytocin), 529-538, (1995).

Rotella, et al., *Journal of Medicinal Chemistry*, "N-3-Substituted Imidazoquinazolinones: Potent and Selective PDE5 Inhibitors as Potential Agents for Treatment of Erectile Dysfunction." vol. 43(7), 1257-1263, (2000).

Truitt, et al.. *Science*. "Identification of a potential ejaculation generator in the spinal cord." vol. 297, 1566-1569, (2002).

Verma et al., *Pharmaceutical Technology On-line*, Drug delivery technologies and future directions, vol. 25(2), 1-14,(2001).

* cited by examiner

SUBSTITUTED TRIAZOLE DERIVATIVES AS OXYTOCIN ANTAGONISTS

The present application is a national stage application under 35 U.S.C. § 371 of PCT International Application No. PCT/IB2006/000602, filed on Mar. 8, 2006, which claims priority from U.S. Provisional Application Ser. No. 60/664,091 filed on Mar. 21, 2005, all of which are herein incorporated by reference in their entirety for all purposes.

The present invention relates to a class of substituted triazoles with activity as oxytocin antagonists, uses thereof, processes for the preparation thereof and compositions containing said inhibitors. These inhibitors have utility in a variety of therapeutic areas including sexual dysfunction, particularly premature ejaculation (P.E.).

International patent applications PCT/IB2004/002977 and PCT/IB2005/000313 disclose substituted triazoles with activity as oxytocin antagonists.

The present invention provides compounds of formula (I)

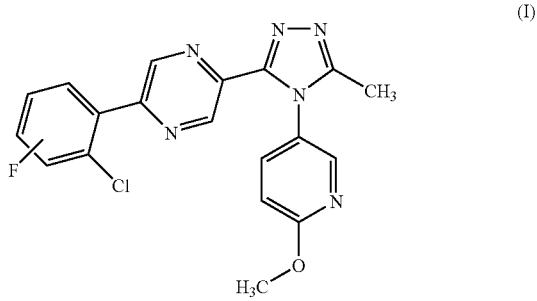

(I)

a tautomer thereof or a pharmaceutically acceptable salt, solvate or polymorph of said compound or tautomer or a prodrug thereof.

In one embodiment the compounds of the invention are 2-(2-Chloro-4-fluoro-phenyl)-5-[4-(6-methoxy-pyridin-3-yl)-5-methyl-4H-[1,2,4]triazol-3-yl]-pyrazine, 2-(2-Chloro-5-fluoro-phenyl)-5-[4-(6-methoxy-pyridin-3-yl)-5-methyl-4H-[1,2,4]triazol-3-yl]-pyrazine, and 2-(2-Chloro-3-fluoro-phenyl)-5-[(4-(6-methoxy-pyridin-3-yl)-5-methyl-4H-[1,2,4]triazol-3-yl]-pyrazine, and tautomers thereof or a pharmaceutically acceptable salt, solvate or polymorph of said compounds or tautomers or a prodrug thereof.

In a particular embodiment, the compound of formula (I) is:

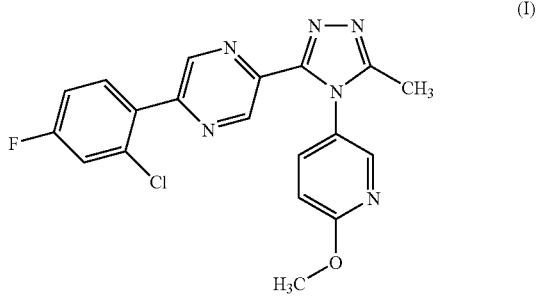

(I)

and tautomers thereof and pharmaceutically acceptable salts, solvates and polymorphs of said compound or tautomer.

In a further embodiment, the compounds of the invention are the compounds of formula (I) and tautomers thereof and pharmaceutically acceptable salts and solvates of said compound and tautomers thereof; in particular the compounds of formula (I) and tautomers thereof and pharmaceutically acceptable salts of said compound and tautomers thereof; more particularly the compounds of formula (I) and tautomers thereof.

Pharmaceutically acceptable salts of the compounds of formula (I) include the acid addition salts thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Hemisalts of acids may also be formed, for example, hemisulphate salts. For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid;
(ii) by removing an acid-labile protecting group from a suitable precursor of the compound of formula (I); or
(iii) by converting one salt of the compound of formula (I) to another by reaction with an appropriate acid or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975). Hereinafter all references to compounds of formula (I) include references to salts, solvates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Also included within the scope of the invention are metabolites of compounds of formula (I), that is, compounds formed in vivo upon administration of the drug. Some examples of metabolites in accordance with the invention include (i) the hydroxymethyl derivative of the methyl group (—$CH_3$→—$CH_2OH$);

(ii) the hydroxy derivative thereof of the methoxy group (—$OCH_3$→—OH); and (iii) a phenol derivative of the phenyl group (—Ph→—PhOH).

In compounds of formula (I) where structural isomers are interconvertible via a low energy barrier, tautomeric isomerism ('tautomerism') can occur. This can take the form of so-called valence tautomerism in compounds which contain an aromatic moiety. Included within the scope of the present invention are all tautomeric forms of the compounds of formula (I).

Also included within the scope of the present invention are optical isomers of the acid addition salts of the compounds of formula (I) wherein the counterion is optically active, for example, d-lactate or l-lysine, or racemic, for example, dl-tartrate or dl-arginine.

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, nitrogen, such as $^{13}N$ and $^{15}N$, and oxygen, such as $^{15}O$, $^{17}O$ and $^{18}O$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of formula (I) as hereinbefore defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of compound of formula (I) which provides the best combination of features for this purpose. Such features include the melting point, solubility, processability and yield of the intermediate form and the resulting ease with which the product may be purified on isolation.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release. Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999). Other means of topical administration include delivery by electroporation, iontophoresis, phonophoresis, sonophoresis and microneedle or needle-free (e.g. Powderject™, Bioject™, etc.) injection. Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying. Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol. Suitable flavours, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 2 to 30 mg of the compound of formula (I). The overall daily dose will typically be in the range 50 to 100 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 50 mg to 100 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly in another aspect the invention provides a pharmaceutical composition comprising a compound of formula (I) or pharmaceutically acceptable salts, solvates or polymorphs thereof, and a pharmaceutically acceptable diluent or carrier.

The compounds of the invention are useful because they have pharmacological activity in mammals, including humans. More particularly, they are useful in the treatment or prevention of a disorder in which modulation of the levels of oxytocin could provide a beneficial effect. Disease states that may be mentioned include sexual dysfunction, particularly premature ejaculation, preterm labour, complications in labour, appetite and feeding disorders, benign prostatic hyperplasia, premature birth, dysmenorrhoea (primary and secondary), congestive heart failure, arterial hypertension, liver cirrhosis, nephrotic hypertension, occular hypertension, obsessive compulsive disorder and neuropsychiatric disorders.

Accordingly in another aspect the invention provides a compound of formula (I) or a pharmaceutically acceptable salt, solvate or polymorph thereof, for use as a medicament.

In another aspect the invention provides a method of treatment of a disorder or condition where inhibition of oxytocin is known, or can be shown, to produce a beneficial effect, in a mammal, comprising administering to said mammal a therapeutically effective amount of a compound of formula (I) or a pharmaceutically acceptable salt, solvate or polymorph thereof.

In another aspect the invention provides the use of a compound of formula (I) or a pharmaceutically acceptable salt, solvate or polymorph thereof, in the preparation of a medicament for the treatment of a disorder or condition where inhibition of oxytocin is known, or can be shown, to produce a beneficial effect.

In another aspect the invention provides a compound of formula (I) or a pharmaceutically acceptable salt, solvate or polymorph thereof, for use in the treatment of a disorder or condition where inhibition of oxytocin is known, or can be shown, to produce a beneficial effect.

In another aspect the invention provides a method of treatment of a disorder or condition where inhibition of oxytocin is known, or can be shown, to produce a beneficial effect, in a mammal, comprising administering to said mammal a therapeutically effective amount of a compound of formula (I) or a pharmaceutically acceptable salt, solvate or polymorph thereof, wherein the disorder or condition is selected from sexual dysfunction, male sexual dysfunction, female sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, occular hypertension, obsessive compulsive disorder and neuropsychiatric disorders.

In another aspect the invention provides the use of a compound of formula (I) or a pharmaceutically acceptable salt, solvate or polymorph thereof, in the preparation of a medicament for the treatment of a disorder or condition where inhibition of oxytocin is known, or can be shown, to produce a beneficial effect, wherein the disorder or condition is selected from sexual dysfunction, male sexual dysfunction, female sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, occular hypertension, obsessive compulsive disorder and neuropsychiatric disorders.

In another aspect the invention provides a compound of formula (I) or a pharmaceutically acceptable salt, solvate or polymorph thereof, for use in the treatment of a disorder or condition where inhibition of oxytocin is known, or can be shown, to produce a beneficial effect, wherein the disorder or condition is selected from sexual dysfunction, male sexual dysfunction, female sexual dysfunction, hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, occular hypertension, obsessive compulsive disorder and neuropsychiatric disorders.

The compounds of the invention are also useful in the treatment or prevention of anxiety, cardiovascular disease (including angina, atherosclerosis, hypertension, heart failure, edema, hypernatremia), inappropriate secretion of vasopressin, endometriosis, emesis (including motion sickness), intrauterine growth retardation, inflammation (including rheumatoid arthritis), mittelschmerz, preclampsia, premature ejaculation, premature (preterm) labor and Raynaud's disease.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al, *J. Urology*, 1999, 161, 5-11).

FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.*, 10, S104-S106; Berman, J. R., Berman, L. & Goldstein, I. (1999). Female sexual dysfunction: Incidence, pathophysiology, evaluations and treatment options. *Urology*, 54, 385-391). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders, *Int. J. Impotence Res.*, 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Thus, in accordance with a further aspect of the invention, there is provided the use of a compound of the invention in the preparation of a medicament for the treatment or prophylaxis of hypoactive sexual desire disorder, sexual arousal disorder, orgasmic disorder and sexual pain disorder, more preferably for the treatment or prophylaxis of sexual arousal disorder, orgasmic disorder, and sexual pain disorder, and most preferably in the treatment or prophylaxis of sexual arousal disorder. Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants eg SSRIs or antihypertensive agents. Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

The Diagnostic and Statistical Manual (DSM) IV of the American Psychiatric Association defines Female Sexual Arousal Disorder (FSAD) as being:

"a persistent or recurrent inability to attain or to maintain until completion of the sexual activity adequate lubrication-swelling response of sexual excitement. The disturbance must cause marked distress or interpersonal difficulty."

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post menopausal (±HRT) women. It is associated with concomitant disorders such as depression, cardiovascular diseases, diabetes and UG disorders. The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

Male sexual dysfunction (MSD) is generally associated with either erectile dysfunction, also known as male erectile dysfunction (MED) and/or ejaculatory disorders such as premature ejaculation, anorgasmia (unable to achieve orgasm) or desire disorders such as hypoactive sexual desire disorder (lack of interest in sex).

PE is a relatively common sexual dysfunction in men. It has been defined in several different ways but the most widely accepted is the Diagnostic and Statistical Manual of Mental Disorders IV one which states:

"PE is a lifelong persistent or recurrent ejaculation with minimal sexual stimulation before, upon or shortly after penetration and before the patient wishes it. The clinician must take into account factors that affect duration of the excitement phase, such as age, novelty of the sexual partner or stimulation, and frequency of sexual activity. The disturbance causes marked distress of interpersonal difficulty."

The International Classification of Diseases 10 definition states:

"There is an inability to delay ejaculation sufficiently to enjoy lovemaking, manifest as either of the following: (1) occurrence of ejaculation before or very soon after the beginning of intercourse (if a time limit is required: before or within 15 seconds of the beginning of intercourse); (2) ejaculation occurs in the absence of sufficient erection to make intercourse possible. The problem is not the result of prolonged abstinence from sexual activity"

Other definitions which have been used include classification on the following criteria:

Related to partner's orgasm

Duration between penetration and ejaculation

Number of thrust and capacity for voluntary control

Psychological factors may be involved in PE, with relationship problems, anxiety, depression, prior sexual failure all playing a role.

Ejaculation is dependent on the sympathetic and parasympathetic nervous systems. Efferent impulses via the sympathetic nervous system to the vas deferens and the epididymis produce smooth muscle contraction, moving sperm into the posterior urethra. Similar contractions of the seminal vesicles, prostatic glands and the bulbourethral glands increase the volume and fluid content of semen. Expulsion of semen is mediated by efferent impulses originating from a population of lumber spinothalamic cells in the lumbosacral spinal cord (Coolen & Truitt, *Science*, 2002, 297, 1566) which pass via the parasympathetic nervous system and cause rhythmic contractions of the bulbocavernous, ischiocavernous and pelvic floor muscles. Cortical control of ejaculation is still under debate in humans. In the rat the medial pre-optic area and the paraventricular nucleus of the hypothalamus seem to be involved in ejaculation.

Ejaculation comprises two separate components—emission and ejaculation. Emission is the deposition of seminal fluid and sperm from the distal epididymis, vas deferens, seminal vesicles and prostrate into the prostatic urethra. Subsequent to this deposition is the forcible expulsion of the seminal contents from the urethral meatus. Ejaculation is distinct from orgasm, which is purely a cerebral event. Often the two processes are coincidental.

A pulse of oxytocin in peripheral serum accompanies ejaculation in mammals. In man oxytocin but not vasopressin plasma concentrations are significantly raised at or around ejaculation. Oxytocin does not induce ejaculation itself; this process is 100% under nervous control via α1-adrenoceptor/sympathetic nerves originating from the lumbar region of the spinal cord. The systemic pulse of oxytocin may have a role in the peripheral ejaculatory response. It could serve to modulate the contraction of ducts and glandular lobules throughout the male genital tract, thus influencing the fluid volume of different ejaculate components for example. Oxytocin released centrally into the brain could influence sexual behaviour, subjective appreciation of arousal (orgasm) and latency to subsequent ejaculation. Accordingly, one aspect of the invention provides for the use of a compound of formula (I) in the preparation of a medicament for the prevention or treatment of sexual dysfunction, preferably male sexual dysfunction, most preferably premature ejaculation.

It has been demonstrated in the scientific literature that the number of oxytocin receptors in the uterus increases during pregnancy, most markedly before the onset of labour (Gimpl & Fahrenholz, 2001, *Physiological Reviews*, 81 (2), 629-683.). Without being bound by any theory it is known that the inhibition of oxytocin can assist in preventing preterm labour and in resolving complications in labour. Accordingly, another aspect of the invention provides for the use of a compound of formula (I) in the preparation of a medicament for the prevention or treatment of preterm labour and complications in labour.

Oxytocin has a role in feeding; it reduces the desire to eat (Arletti et al., *Peptides*, 1989, 10, 89). By inhibiting oxytocin it is possible to increase the desire to eat. Accordingly oxytocin inhibitors are useful in treating appetite and feeding disorders. Accordingly, a further aspect of the invention provides for the use of a compound of formula (I) in the preparation of a medicament for the prevention or treatment of appetite and feeding disorders.

Oxytocin is implicated as one of the causes of benign prostatic hyperplasia (BPH). Analysis of prostate tissue have shown that patients with BPH have increased levels of oxytocin (Nicholson & Jenkin, *Adv. Exp. Med. & Biol.*, 1995, 395, 529). Oxytocin antagonists can help treat this condition. Accordingly, another aspect of the invention provides for the use of a compound of formula (I) in the preparation of a medicament for the prevention or treatment of benign prostatic hyperplasia.

Oxytocin has a role in the causes of dysmenorrhoea due to its activity as a uterine vasoconstrictor (Akerlund, *Ann. NY Acad. Sci.*, 1994, 734, 47). Oxytocin antagonists can have a therapeutic effect on this condition. Accordingly, a further aspect of the invention provides for the use of a compound of formula (I) in the preparation of a medicament for the prevention of treatment of dysmenorrhoea.

It is to be appreciated that all references herein to treatment include curative, palliative and prophylactic treatment.

The compounds of the present invention may be coadministered with one or more agents selected from:

1) One or more selective serotonin reuptake inhibitors (SSRIs) such as dapoxetine, paroxetine, 3-[(dimethylamino)methyl]-4-[4-(methylsulfanyl)phenoxy]benzenesulfonamide (Example 28, WO 0172687), 3-[(dimethylamino)methyl]-4-[3-methyl-4-(methylsulfanyl)phenoxy] benzenesulfonamide (Example 12, WO 0218333), N-methyl-N-({3-[3-methyl-4-(methylsulfanyl)phenoxy]-4-pyridinyl}methyl)amine (Example 38, PCT Application no PCT/IB02/01032).

2) One or more local anaesthetics;

3) one or more α-adrenergic receptor antagonists (also known as α-adrenoceptor blockers, α-receptor blockers or α-blockers); suitable $\alpha_1$-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, Example 19 of WO9830560, terazosin and abanoquil; suitable $\alpha_2$-adrenergic receptor antagonists include dibenamine, tolazoline, trimazosin, efaroxan, yohimbine, idazoxan clonidine and dibenamine; suitable non-selective α-adrenergic receptor antagonists include dapiprazole; further α-adrenergic receptor antagonists are described in PCT application WO99/30697 published on 14 Jun. 1998 and U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference;

4) one or more cholesterol lowering agents such as statins (e.g. atorvastatin/Lipitor—trade mark) and fibrates;

5) one or more of a serotonin receptor agonist, antagonist or modulator, more particularly agonists, antagonists or modulators for example 5HT1A, 5HT2A, 5HT2C, 5HT3, 5HT6 and/or 5HT7 receptors, including those described in WO-09902159, WO-00002550 and/or WO-00028993;

6) one or more NEP inhibitors, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; IC50 values against NEP and ACE may be determined using methods described in published patent application EP1097719-A1, paragraphs [0368] to [0376];

7) one or more of an antagonist or modulator for vasopressin receptors, such as relcovaptan (SR 49059), conivaptan, atosiban, VPA-985, CL-385004, Vasotocin.

8) Apomorphine—teachings on the use of apomorphine as a pharmaceutical may be found in U.S. Pat. No. 5,945,117;

9) Dopamine agonists (in particular selective D2, selective D3, selective D4 and selective D2-like agents) such as Pramipexole (Pharmacia Upjohn compound number PNU95666), ropinirole, apomorphine, surmanirole, quinelorane, PNU-142774, bromocriptine, carbergoline, Lisuride;

10) Melanocortin receptor agonists (e.g. Melanotan II and PT141) and selective MC3 and MC4 agonists (e.g. THIQ);
11) Mono amine transport inhibitors, particularly Noradrenaline Re-uptake Inhibitors (NRIs) (e.g. Reboxetine), other Serotonin Re-uptake Inhibitors (SRIs) (e.g. paroxetine, dapoxetine) or Dopamine Re-uptake Inhibitors (DRIs);
12) 5-HT$_{1A}$ antagonists (e.g. robalzotan); and
13) PDE inhibitors such as PDE2 (e.g. erythro-9-(2-hydroxyl-3-nonyl)-adenine) and Example 100 of EP 0771799-incorporated herein by reference) and in particular a PDE5 inhibitor such as the pyrazolo[4,3-d]pyrimidin-7-ones disclosed in EP-A-0463756; the pyrazolo[4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido[3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO 99/54333; the pyrazolo[4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124. The pyrazolo[4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclosed in EP-A-1092719.

Preferred PDE5 inhibitors for use with the invention:
5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);
5-(2-ethoxy-5-morpholinoacetylphenyl)-1-methyl-3-n-propyl-1,6-dihydro-7H-pyrazolo[4,3-d]pyrimidin-7-one (see EP-A-0526004);
3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);
3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);
(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);
5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);
5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);
5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);
5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);
5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);
(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8;
2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and
the compound of example 11 of published international application WO93/07124 (EISAI); and compounds 3 and 14 from Rotella D P, J. Med. Chem., 2000, 43, 1257.

Still further PDE5 inhibitors for use with the invention include:
4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furaziocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5 (5-morpholinoacetyl-2-n-propoxyphenyl)-3-n-propyl-1, 6-dihydro-7H-pyrazolo(4,3-d)pyrimidin-7-one; 1-[4-[(1, 3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

The contents of the published patent applications and journal articles and in particular the general formulae of the therapeutically active compounds of the claims and exemplified compounds therein are incorporated herein in their entirety by reference thereto.

More preferred PDE5 inhibitors for use with the invention are selected from the group:
5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one or 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof.

A particularly preferred PDE5 inhibitor is 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) (also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine) and pharmaceutically acceptable salts thereof. Sildenafil citrate is a preferred salt.

Preferred agents for coadministration with the compounds of the present invention are PDE5 inhibitors, selective serotonin reuptake inhibitors (SSRIs), vasopressin $V_{1A}$ antagonists, α-adrenergic receptor antagonists, NEP inhibitors, dopamine agonists and melanocortin receptor agonists as described above. Particularly preferred agents for coadministration are PDE5 inhibitors, SSRIs, and $V_{1A}$ antagonists as described herein.

A suitable assay for determining the oxytocin antagonist activity of a compound is detailed herein below.

Oxytocin Receptor Beta-Lactamase Assay

Materials:

Cell Culture/Reagents

| A: cell culture | B: reagents |
|---|---|
| Nutrient Mixture | Oxytocin |
| F12 Ham's | OT receptor-specific antagonist |
| Foetal Bovine Serum (FBS) | Molecular grade Dimethyl Sulphoxide (DMSO) |
| Geneticin | Trypan Blue Solution 0.4% |
| Zeocin | CCF4-AM (Solution A) |
| Trypsin/EDTA | Pluronic F127s (Solution B) |
| PBS (phosphate buffered saline) | 24% PEG, 18% TR40 (Solution C) |
| HEPES | Probenecid (Dissolved at 200 mM in 200 mM NaOH, Solution D) |

Methods:

Cell Culture

Cells used are CHO-OTR/NFAT-β-Lactamase. The NFAT-β-lactamase expression construct was transfected into the CHO-OTR cell line and clonal populations were isolated via fluorescence activated cell sorting (FACS). An appropriate clone was selected to develop the assay.

| Growth Medium | Assay media |
|---|---|
| 90% F12 Nutrient Mix, 15 mM HEPES 10% FBS | 99.5% F12 Nutrient Mix, 15 mM HEPES 0.5% FBS |
| 400 µg/ml Geneticin 200 µg/ml Zeocin 2 mM L-Glutamine | |

Recovery of cells—A vial of frozen cells is thawed rapidly in 37° C. water bath and the cell suspension transferred into a T225 flask with 50 ml of fresh growth medium and then incubated at 37° C., 5% $CO_2$ in an incubator until the cells adhered to the flask Replace media with 50 ml of fresh growth media the following day. Culturing cells—CHO-OTR-NFAT-βLactamase cells were grown in growth medium. Cells were harvested when they reached 80-90% confluence removing the medium and washing with pre-warmed PBS. PBS was then removed and Trypsin/EDTA added (3 mls for T225 cm² flask) before incubating for 5 min in 37° C./5% $CO_2$ incubator. When cells were detached, pre-warmed growth media was added (7 mls for T225 cm² flask) and the cells re-suspended and mixed gently by pipetting to achieve single cell suspension. The cells were split into T225 flask at 1:10 (for 3 days growth) and 1:30 (for 5 days growth) ratio in 35 ml growth medium.

β-Lactamase Assay Method

Day 1

Cell Plate Preparation:

Cells grown at 80-90% confluence were harvested and counted. Suspensions of cells at 2×105 cells/ml in growth medium were prepared and 30 µl of cells suspension added in 384-well, black clear-bottom plates. A blank plate containing diluents from each reagent was used for background subtraction. Plates were incubated at 37° C., 5% $CO_2$ overnight.

Day 2

Cells Stimulation:

10 µl antagonist/compound (diluted in assay media containing 1.25% DMSO=antagonist diluent) was added to appropriate wells and incubated for 15 minutes at 37° C., 5% $CO_2$.

10 µl oxytocin, made up in assay media, was added to all wells and incubated for 4 hours at 37° C., 5% $CO_2$.

A separate 384-well cell plate was used to generate an oxytocin dose response curve. (10 µl antagonist diluent was added to every well. 10 µl of oxytocin was then added. The cells are then treated as per antagonist/compound cell plates).

Preparation of 1 ml of 6× Loading Buffer with Enhanced Loading Protocol (this requires scale-up according to number of plates to be screened)

12 µl of solution A (1 mM CCF4-AM in Dry DMSO) was added to 60 µl of solution B (100 mg/ml Pluronic-F127 in DMSO+0.1% Acetic Acid) and vortexed.

The resulting solution was added to 9251 of solution C (24% w/w PEG400, 18% TR40 v/v in water).

75 µl of solution D was added (200 mM probenecid in 200 mM NaOH).

10 µl of 6× Loading Buffer was added to all wells and incubated for 1.5 hrs-2 hrs at room temperature in the dark.

The plates were read using an LJL Analyst, Excitation 405 nm, Emission 450 nm and 530 nm, gain optimal, lagtime 0.40 µs integration, 4 flashes, bottom reading.

The compound of Example 1 has a Ki value of 5.4 nM (n=3).

The invention is illustrated by the following non-limiting examples in which the following abbreviations and definitions are used:

| | |
|---|---|
| APCI+ | Atmospheric Pressure Chemical Ionisation (positive scan) |
| bs | Broad singlet |
| CDCl$_3$ | Chloroform-d1 |
| d | Doublet |
| dd | Doublet of doublets |
| DMSO | Dimethylsulfoxide |
| ES+ | Electrospray ionisation positive scan. |
| eq | Equivalent |
| $^1$H NMR | Proton Nuclear Magnetic Resonance Spectroscopy |
| MS | (Low Resolution) Mass Spectroscopy |
| m | Multiplet |
| m/z | Mass spectrum peak |
| q | Quartet |
| s | Singlet |
| t | Triplet |
| δ | Chemical shift |

Preparation 1 di-μ-Chlorobis[2-[(dimethylamino-κN)methyl]phenyl-κC]di-palladium

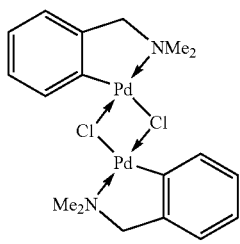

To a suspension of palladium chloride (3.43 g, 19.4 mmol) in methanol (200 mL) under nitrogen at room temperature was added N,N-dimethylbenzylamine (5.82 mL, 38.7 mmol) via syringe. The resulting red/brown suspension was stirred at room temperature for 24 hours. The now green/brown suspension was concentrated in vacuo to remove methanol, redissolved in dichloromethane (150 mL) and passed through a pad of silica gel washing through with dichloromethane. The resulting bright yellow filtrate was concentrated in vacuo and recrystallised from dichloromethane:ether to yield the title compound, 4.66 g. $^1$H NMR (CDCl$_3$, 300 MHz) δ: 2.86 (s, 6H), 2.89 (s, 6H), 3.95 (s, 4H), 6.84-7.24 (m, 8H)

Preparation 2 bis[2-[(Dimethylamino-κN)methyl]phenyl-κC]bis[μ-(trifluoroacetato-κO:κO')]-palladium

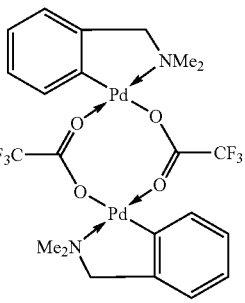

To a solution of silver trifluoroacetate (4.48 g, 20.3 mmol) in acetone (30 mL) under nitrogen at room temperature was added a solution of the complex of preparation 1 (5.60 g, 10.15 mmol) in dichloromethane (100 mL). A thick white precipitate appeared during addition. The suspension was stirred for 15 minutes, and was then filtered through a pad of silica gel, washing with dichloromethane. Concentration in vacuo gave a bright yellow powder that was recrystallised from dichloromethane:ether to yield the title compound, 7.06 g. $^1$H NMR (CDCl$_3$, 300 MHz) δ: 2.05 (s, 6H), 2.88 (s, 6H), 3.18 (d, 2H), 3.63 (d, 2H), 6.89-6.97 (m, 6H), 7.00-7.10 (m, 2H)

Preparation 3

[2-[(Dimethylamino-κN)methyl]phenyl-κC](tricyclohexylphosphine)(trifluoroacetato-κO-(SP-4-3)-palladium

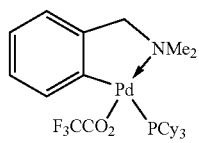

To a solution of the product of preparation 2 (6.43 g, 9.10 mmol) in dichloromethane (50 mL) under nitrogen at room temperature was added a solution of tricyclohexylphosphine (6.89 g, 24.5 mmol) in dichloromethane (20 mL). After stirring for 1 hour, the solution was passed through a plug of silica gel (7 cm×2 cm) washing with dichloromethane (400 mL), and the pale yellow filtrate concentrated in vacuo. Recrystallisation from dichloromethane:ether yielded the title compound, 10.53 g. $^1$H NMR (CDCl$_3$, 300 MHz) δ:

1.05-2.30 (m, 33H), 2.57 (s, 3H), 2.58 (s, 3H), 3.93 (s, 2H), 6.86-6.98 (m, 3H), 7.10-7.12 (m, 1H)

Preparation 4

5-Chloro-pyrazine-2-carboxylic acid hydrazide

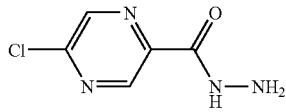

5-chloro-pyrazine-2-carboxylic acid methyl ester (10.02 g, 58.25 mmol) and hydrazine monohydrate (12.5 mL, 250 mmol) were dissolved in methanol (400 mL) and the reaction mixture heated to reflux for 48 hours. The reaction mixture was then filtered and the precipitate collected dried in vacuo to yield the title compound, 5.01 g (50%).
$^1$H NMR (CDCl$_3$, 400 MHz) δ: 4.09 (d, 2H), 8.52 (s, 1H), 8.66 (bs, 1H), 9.14 (s, 1H). Microanalysis: C$_5$H$_5$ClN$_4$O requires: C, 34.80; H, 2.92; N, 32.47. found C, 34.89; H, 2.91, N, 32.32. MS APCI+ m/z 173 [MH]$^+$ Preparation 5

5-Chloro-pyrazine-2-carboxylic acid N'-acetyl-hydrazide

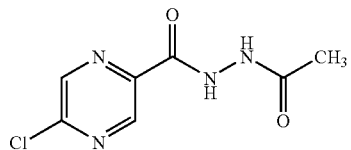

The product of preparation 4 (2.0 g, 29.2 mmol) and N-methylmorpholine (1.8 mL, 35 mmol) were dissolved in dichloromethane (100 mL) and the solution treated with acetyl chloride (1.04 mL, 11.4 mmol). The reaction mixture was stirred at room temperature for 5 hours and then washed with water and concentrated in vacuo to yield the title compound 4.0 g, (64%). MS APCI+ m/z 215 [MH]$^+$ Preparation 6

2-Chloro-5-(5-methyl-[1,3,4]oxadiazol-2-yl)-pyrazine

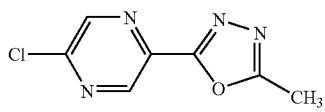

The product of preparation 5 (125 g, 435.1 mmol) and phosphorous oxychloride (250 mL) were combined and heated to 110° C. for 4 hours. The reaction mixture was concentrated in vacuo and the residue taken up in ethyl acetate and water. The mixture was neutralised by the addition of 10% sodium carbonate solution and the phases separated. The aqueous phase was extracted with ethyl acetate and the combined organics dried over magnesium sulfate and concentrated in vacuo. The residue was purified by column chromatography on silica gel eluting with ethyl acetate to yield the title compound, 30 g, (35%).
$^1$H NMR (CDCl$_3$, 400 MHz) δ: 2.68 (s, 3H), 8.71 (s, 1H), 9.22 (s, 1H). MS APCI+ m/z 197 [MH]$^+$ Preparation 7

2-Chloro-5-[4-(6-methoxy-pyridin-3-yl)-5-methyl-4H-[1,2,4]triazol-3-yl]-pyrazine

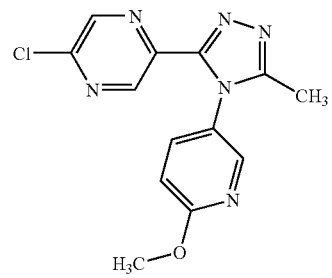

The product of preparation 6 (8.73 g, 32.3 mmol), 5-amino-2-methoxypyridine (12 g, 96.7 mmol) and para-toluenesulfonic acid monohydrate (50 mg, 0.37 mmol) were dissolved in xylene (100 mL) and the reaction mixture heated to 150° C. for 23 hours. The reaction mixture was concentrated in vacuo and the residue purified by column chromatography on silica gel eluting with dichloromethane:methanol 100:0 to 90:10 to yield the title compound, 4.3 g, (44%).
$^1$H NMR (CDCl$_3$, 400 MHz) δ: 2.36 (s, 3H), 3.99 (s, 3H), 6.86 (d, 1H), 7.45 (dd, 1H), 8.02 (d, 1H), 8.27 (d, 1H), 9.23 (d, 1H).

Preparation 8

2-(2-chloro-3-fluorophenyl)-4,4',5,5'-tetramethyl-1,3,2-dioxoborolane

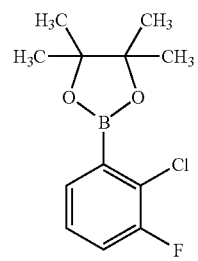

A solution of Bis(pinacolato)diboron (1.27 g, 5.0 mmol) in dimethylformamide (10 mL) had nitrogen gas bubbled through for ~30 mins. 1-bromo-2-chloro-3-fluorobenzene, palladium (II) acetate and potassium acetate were added and the mixture heated to 80° C. for 1.5 hours. The reaction mixture was concentrated in vacuo and the residue taken up in ethyl acetate and water. The organic layer was washed with brine and the organic layer dried over magnesium sulfate and concentrated in vacuo. The residue was purified by column chromatography on silica gel eluting with pentane:ethyl acetate 100:0 to 95:5 to yield the title compound, 530 mg, (34%). $^1$H NMR (DMSO, 400 MHz) δ: 1.32 (s, 12H), 7.35-7.52 (m, 3H).

EXAMPLE 1

2-(2-Chloro-4-fluoro-phenyl)-5-[4-(6-methoxy-pyridin-3-yl)-5-methyl-4H-[1,2,4]triazol-3-yl]-pyrazine

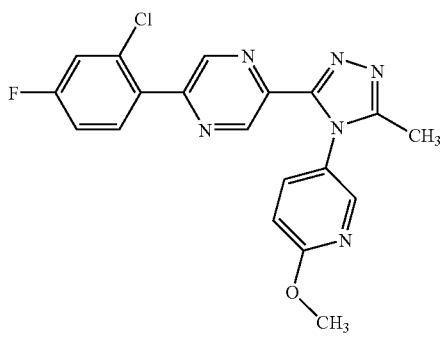

The chloro compound of preparation 7 (150 mg, 0.50 mmol), 2-chloro-4-fluorophenyl boronic acid (130 mg, 0.75 mmol) and the palladium complex of preparation 3 (10 mg) were dissolved in dioxane (10 mL) and the solution was treated with ceasium carbonate (484 mg, 01.49 mmol). The reaction mixture was heated to reflux for 4.5 hours and then concentrated in vacuo. The residue was taken up in ethyl acetate (25 mL) and washed with water (25 mL), 2M sodium hydroxide solution (25 mL) and brine (25 mL). The solution was dried over magnesium sulfate and concentrated in vacuo. The residue was purified by column chromatography on silica gel eluting with dichloromethane:methanol 100:0 to 95:5 to yield the title compound, 53 mg, (27%). $^1$H NMR (CDCl$_3$, 400 MHz) δ: 2.42 (s, 3H), 4.00 (s, 3H), 6.89 (d, 1H), 7.13 (m, 1H), 7.24 (m, 1H), 7.52 (m, 1H), 7.64 (m, 1H), 8.08 (d, 1H), 8.67 (d, 1H), 9.52 (d, 1H). MS ES+ m/z 399 [MH]$^+$

EXAMPLE 2

2-(2-Chloro-5-fluoro-phenyl)-5-[4-(6-methoxy-pyridin-3-yl)-5-methyl-4H-[1,2,4]triazol-3-yl]-pyrazine

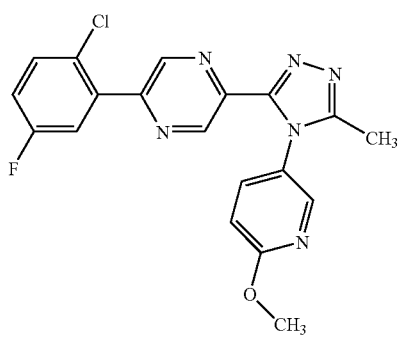

This example was prepared using the same method as described for Example 1 with 2-chloro-5-fluorophenyl boronic acid to yield the title compound as a white solid, 12 mg (6%). $^1$H NMR (CDCl$_3$, 400 MHz) δ: 2.38 (s, 3H), 4.00 (s, 3H), 6.88 (d, 1H), 7.10 (m, 1H), 7.39 (m, 1H), 7.44 (m, 1H), 7.50 (m, 1H), 8.07 (d, 1H), 8.70 (d, 1H), 9.54 (d, 1H). MS ES+ m/z 399 [MH]$^+$

EXAMPLE 3

2-(2-Chloro-3-fluoro-phenyl)-5-[4-(6-methoxy-pyridin-3-yl)-5-methyl-4H-[1,2,4]triazol-3-yl]-pyrazine

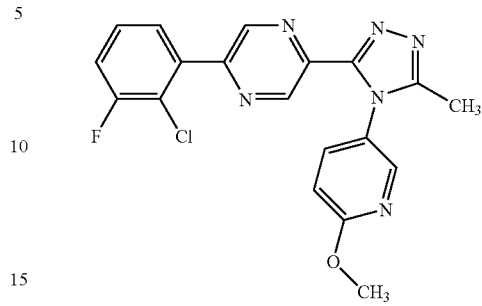

This example was prepared using the same method as described for Example 1 using the compound of preparation 8 to yield the title compound as a white solid, 48 mg (36%). $^1$H NMR (CDCl$_3$, 400 MHz) δ: 2.46 (s, 3H), 4.03 (s, 3H), 6.91 (d, 1H), 7.25-7.30 (m, 1H), 7.38 (m, 1H), 7.45 (d, 1H), 7.57 (dd, 1H), 8.12 (d, 1H), 8.69 (d, 1H), 9.57 (d, 1H). MS APCI+ m/z 399 [MH]$^+$.

The invention claimed is:
1. A compound of formula (I)

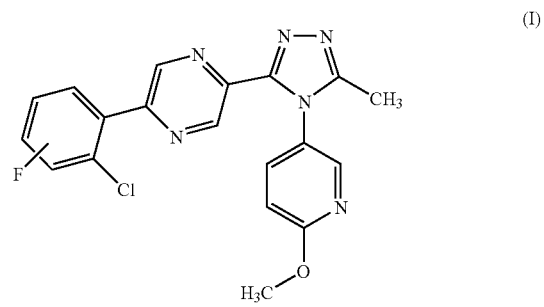

(I)

or a tautomer thereof or a pharmaceutically acceptable salt of said compound or tautomer.

2. The compound according to claim 1 of the formula

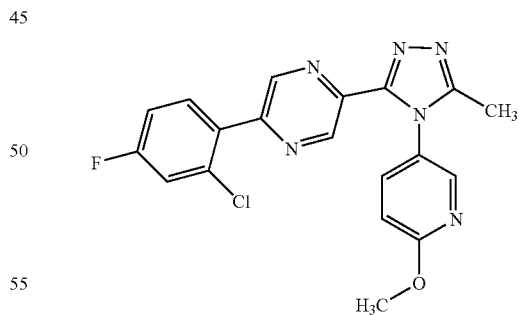

or a tautomer thereof or a pharmaceutically acceptable salt of said compound or tautomer.

3. A pharmaceutical composition comprising a compound according to claim 1 or claim 2, or a pharmaceutically acceptable salt thereof, and a pharmaceutically acceptable diluent or carrier.

* * * * *